United States Patent
Paul et al.

[11] 4,031,783
[45] June 28, 1977

[54] TATTOO ETCHING MACHINE

[76] Inventors: Stanley C. Paul; Shelby J. Russell, both of 9912 Woodside, Detroit, Mich. 48204

[22] Filed: Apr. 7, 1975

[21] Appl. No.: 565,342

[52] U.S. Cl. .............................................. 81/9.22
[51] Int. Cl.² .......................................... B26F 1/24
[58] Field of Search .............. 81/9.22; 30/362, 366

[56] References Cited
UNITED STATES PATENTS

| 203,329 | 5/1878 | Edison | 30/362 |
| 205,370 | 6/1878 | Edison | 30/362 |
| 917,146 | 4/1909 | Ramsay | 30/362 |
| 990,786 | 4/1911 | Selig | 30/362 |
| 1,767,469 | 6/1930 | Metzner | 81/9.22 |

FOREIGN PATENTS OR APPLICATIONS 598,451   12/1925   France .............................. 30/362

*Primary Examiner*—Al Lawrence Smith
*Assistant Examiner*—Roscoe V. Parker
*Attorney, Agent, or Firm*—Whittemore, Hulbert & Belknap

[57] ABSTRACT

A tattoo etching machine including eccentric needle drive structure for reciprocating a tattoo needle, a motor and flexible cable for remotely driving the eccentric drive structure, adjustable length barrel and frictionally secured cover.

1 Claim, 3 Drawing Figures

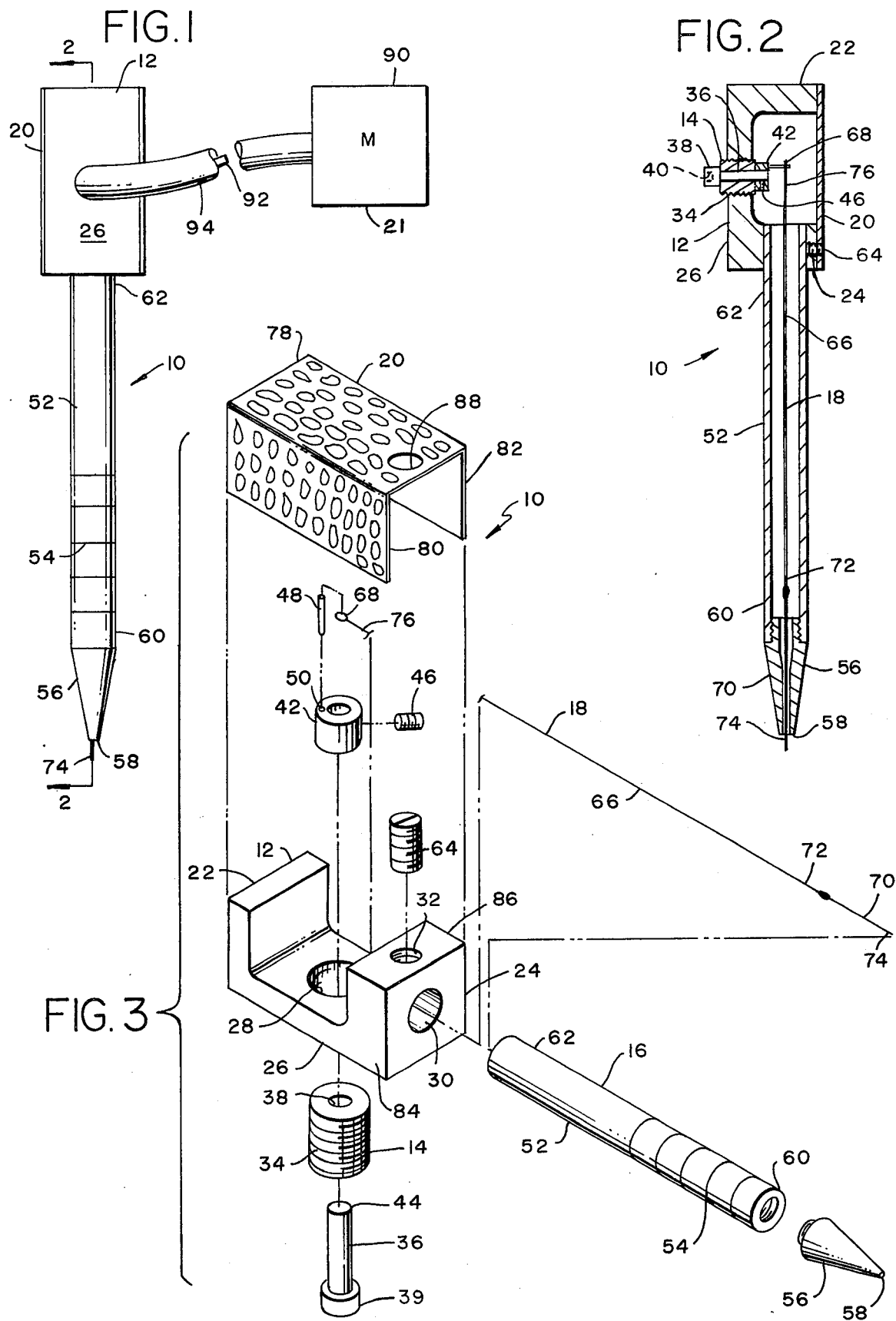

TATTOO ETCHING MACHINE

BACKGROUND OF THE INVENTION

1. Field of the Invention

The invention refers specifically to a tattoo etching machine for effecting ink drawings on skin and refers more specifically to a tattoo machine which includes a tattoo needle which is reciprocally guided within a tattoo machine barrel by eccentric pin needle drive means which is remotely driven to provide an extremely light, well-balanced tattoo pin not subject to overheating or electrical shock and which is quiet in operation, particularly simple in design, economical to construct and efficient in use.

2. Description of the Prior Art

In the past, tattoo etching machines have generally been driven by electical means such as coils which alternately attract and release tattoo needle structure, which needle structure has been spring-biased to extend out of a tattoo pin barrel. Due to the necessity of having the electric coils which effect the reciprocation of the needles within the prior tattoo machines, the machines have been heavy, have had a tendency to overheat and have been noisy in operation. In addition, with the prior structure, there has been a possibility of electric shock being transmitted therefrom due to malfunction of the necessary electrical connection thereto.

SUMMARY OF THE INVENTION

In accordance with the invention, there is provided a tattoo etching machine which includes eccentric pin drive structure for reciprocating as tattoo needle. The eccentric pin drive structure is remotely driven through a flexible cable.

The barrel of the tattoo machine of the invention is adjustable to determine the degree of extension of the tattoo needle from the barrel during reciprocation of the needle. The operating mechanism of the tattoo pin is completely enclosed with cover structure which requires no fasteners, which is readily releasable to permit maintenance of and/or adjustment of the drive structure and which permits axial adjustment of the barrel of the tattoo machine with the cover in place.

BRIEF DESCRIPTION OF THE DRAWINGS

FIG. 1 is an elevation view of a tattoo etching machine constructed in accordance with the invention.

FIG. 2 is a section view of the tattoo etching machine illustrated in FIG. 1, taken substantially on the line 2—2 of FIG. 1.

FIG. 3 is an exploded isometric view of the elements of the tattoo etching machine of FIGS. 1 and 2.

DESCRIPTION OF THE PREFERRED EMBODIMENT

As shown best in FIG. 3, the tattoo etching machine 10 includes a body member 12, eccentric pin drive structure 14, barrel structure 16, needle structure 18, cover 20 and remote drive structure 21.

The body member 12, as shown, is generally U-shaped and includes a top leg portion 22, bottom leg portion 24 and connecting portion 26. A threaded opening 28 extends through the connecting portion 26 of the body member, a non-threaded opening 30 and a threaded opening 32 extend through the bottom leg portion 24 of the body member 12 at right angles to each other, as shown best in FIG. 3.

The eccentric pin drive structure 14 includes a threaded drive coupling bearing member 34 adapted to be threaded in the opening 28 in the body member 12, a drive shaft 36 which extends through the opening 38 in the bearing member 34 and is rotatable therein. Needle bearings may be placed between the member 34 and drive shaft 36, if desired. The drive shaft 36 includes means at the end 39 thereof for coupling the drive shaft 36 to means for rotating the drive shaft, such as a non-circular recess 40 therein for receiving a non-circular end of flexible cable 92.

The eccentric pin drive structure 14 further includes a hollow cylindrical member 42 which is secured on the end 44 of the drive shaft 36 after it has been passed through the opening 38 of the bearing member 34 by convenient means such as set screw 46 or by being pressed on. A pin 48 is secured in opening 50 in the hollow cylindrical member 42 as by being pressed in the opening 50. The longitudinal axis of the pin 48 is eccentric with respect to the axis of rotation of the drive shaft 36 and thus forms a circle having the radius of the eccentricity on rotation of the drive shaft.

The barrel means 16 includes the hollow cylindrical barrel 52 which may have knurling 54 on the exterior surface to facilitate gripping thereof, if desired, and the barrel tip 56 having the opening 58 therethrough through which the needle means 18 may extend. The barrel tip 56 as shown is secured to the end 60 of the barrel 52 by mating threads on the interior of the end 60 of the barrel 52 and on the barrel tip 56. Alternatively, the barrel tip may be constructed integrally with the barrel.

The other end 62 of the barrel 52 is adapted to be adjustably positioned in the opening 30 in the body member 12 and is secured in longitudinally adjusted positions in the opening 30 by the set screw 64 threaded in the opening 32 in the body member 12. Screw 64 may be readily adjusted through the opening 88 in the cover 20.

The needle means 18 includes the needle bar 66 having an eye 68 in one end thereof which is connected by convenient means such as solder to the tattooing needle 70 at the other end 72 thereof. The needle means 66 extends through the opening 30, the barrel 52 and barrel tip 56 so that the needle end 74 will extend through the opening 58 in the barrel tip 56 in one axial position thereof a predetermined amount. The eye 68 on the one end 76 of the needle bar 66 is in assembly passed over the eccentric pin 48 whereby as the pin moves in its circular motion on rotation of the drive shaft 36, the needle means is caused to reciprocate substantially axially at least at the end 74 of the needle 70 to produce movement of the needle end 74 into and out of the opening 58 in the barrel tip 56 an amount and at a speed depending on the speed of rotation of the shaft 36 and the adjusted position of the barrel 52.

The cover 20 of the tattoo etching machine 10 is a generally U-shaped member having the connecting portion 78 and the side portions 80 and 82. The cover 20 is made of resilient material such as spring metal and the sides 80 and 82 are constructed so as to converge slightly, outwardly of the connecting portion 78 so that on placement of the cover 20 over the body member 12, the sides 80 and 82 must be spread apart against the resiliency of the material of which the cover 20 is made. Accordingly, the sides 80 and 82 grip the sides 84 and 86, respectively, of the body member 12, and the cover 20 is thus held in place on the body member 12. An opening 88 is provided in the cover 20 to permit adjustment of the position of the barrel 52 by means of the set screw 64 as desired with the cover in place. Should it be desired to adjust the eccentric drive structure 14 from inside the body member 12, the cover 20 may be easily slipped off and subsequently replaced on the body member 12.

As shown best in FIG. 1, the drive shaft 36 is driven by remote drive structure 21 including motor means 90 which may be any of a number of different type motors such as electric, hydraulic or pneumatic, and which produces rotation of the flexible cable 92 having the protective cover 94 thereon.

In overall operation of the tattoo etching machine of the invention with the elements thereof as shown in FIG. 3, assembled as shown in FIGS. 1 and 2, the end 74 of the needle 70 is dipped in ink, the tattoo etching machine is held in the hand of a tattoo artist over a portion of skin to be colored in accordance with the ink on the needle, and the motor is started to rotate the cable 92. The cable 92 causes the shaft 36 to rotate, ultimately causing the pin 48 to rotate to reciprocate the needle means 18 in the barrel 52 to cause the end 74 of needle 70 to move into and out of the opening 58 in barrel tip 56 and to perforate the skin and thus leave ink from the needle in the skin to color the skin in any design in accordance with the manipulation of the tattoo machine by the tattoo artist.

While one embodiment of the invention has been considered in detail, it will be understood that other embodiments and modifications thereof are contemplated. Thus, for example, it will be possible to use any of the known tattooing techniques, including those requiring a different number of needles, and different length of extension of the needle from the barrel tip, with the tattoo etching machine of the invention. It is intended to include all embodiments and modifications as are defined by the appended claims within the scope of the invention.

What we claim as our invention is:

1. A tattoo etching machine comprising a U-shaped body member having a top leg portion and a bottom leg portion, each connected at one end to a connecting portion, which body member has a threaded opening in the connecting portion extending in the direction of the leg portions, a non-threaded opening in the bottom leg portion extending transversely of the leg portions and in the direction of the connecting portion, and a threaded opening extending from the free end of the bottom leg portion in the direction of the bottom leg portion into the non-threaded opening therethrough, an externally threaded bearing member positioned within the threaded opening in the connecting portion of the body member having a cylindrical opening extending axially thereof, a drive shaft having a head on one end thereof extending through the opening in the bearing member for rotation therein, means for connecting a drive cable to the one end of the drive shaft exteriorly of the body member, a hollow cylinder having a radially extending threaded opening extending transversely therethrough sleeved over the other end of the drive shaft within the body member between the leg portions thereof for rotation with the drive shaft, a set screw extending through the radial opening in the hollow cylinder rigidly securing the cylinder to the drive shaft, a pin extending axially of the drive shaft from the hollow cylindrical member and offset from the axis of rotation of the hollow cylindrical member and the drive shaft, a hollow cylindrical barrel one end of which extends through the unthreaded opening in the bottom leg portion of the body member transversely of the bottom leg portion and in the direction of the connecting portion of the body member, a barrel tip secured to the other end of the barrel having an opening therethrough extending axially of the barrel, needle means extending through the barrel, one end of which is adapted to extend through the opening in the barrel tip in one position of the needle means and the other end of which includes an opening therethrough through which the pin on the cylinder secured to the drive shaft passes, whereby on rotation of the drive shaft the needle means is reciprocated into and out of the opening in the barrel tip a controlled distance, a threaded set screw extending through the opening in the bottom leg portion of the body member and into contact with the one end of the barrel for securing the barrel to the body member in axially adjusted positions of the barrel with respect to the body member, and a cover for the body member enclosing the area between the top and bottom leg portions of the body member, which cover is a U-shaped member constructed of resilient material having a connecting portion and a pair of leg portions, which leg portions converge slightly toward each other with the cover not assembled on the body portion, whereby on assembly of the cover with the body portion the leg portions are spread apart and the resiliency of the cover material holds the cover on the body member.

* * * * *